Figure 3A:
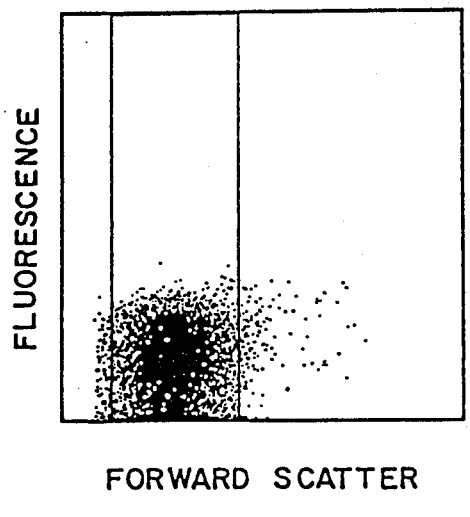

United States Patent [19]

Lee et al.

[11] Patent Number: 4,883,867
[45] Date of Patent: Nov. 28, 1989

[54] DETECTION OF RETICULOCYTES, RNA OR DNA

[75] Inventors: Linda G. Lee, Mountain View; Chia-Huei Chen, San Jose, both of Calif.

[73] Assignee: Becton, Dickinson and Company, Franklin Lakes, N.J.

[21] Appl. No.: 81,097

[22] Filed: Aug. 3, 1987

Related U.S. Application Data

[63] Continuation-in-part of Ser. No. 793,813, Nov. 1, 1985, abandoned.

[51] Int. Cl.⁴ .................. C07H 15/12; C07H 17/00; G01N 31/00; G01N 33/48
[52] U.S. Cl. .......................... 536/28; 436/63; 436/10; 436/94; 436/172; 436/800; 536/27
[58] Field of Search ............... 250/461; 546/152, 166, 546/176; 548/146; 435/4, 6; 436/63, 72, 800, 10, 94, 172; 424/3, 7.1, 9; 356/39; 536/28

[56] References Cited

U.S. PATENT DOCUMENTS

| 3,615,637 | 10/1971 | Shiba et al. | 430/576 |
|---|---|---|---|
| 3,872,312 | 3/1975 | Hirschfeld | 250/461.2 |
| 4,108,668 | 8/1978 | Sakazume et al. | 430/586 |
| 4,134,767 | 1/1979 | Sakazume et al. | 430/384 |
| 4,193,980 | 3/1980 | Clason | 436/63 |
| 4,273,862 | 6/1981 | Yoshida et al. | 430/586 |
| 4,325,706 | 4/1982 | Gershman et al. | 424/3 |
| 4,544,546 | 10/1985 | Wang et al. | 424/3 |
| 4,571,388 | 2/1986 | O'Connell et al. | 436/63 |
| 4,585,736 | 4/1986 | Dolbeare et al. | 436/63 |

FOREIGN PATENT DOCUMENTS

0004061  7/1979  European Pat. Off. ............ 424/3

OTHER PUBLICATIONS

Chem. Abs. 73:125723 (6/70).
Chem Abs. 83:50699 (1/75).
Chem. Abs. 86:148784 (10/76).
Venkataraman K.; Academic Press, N.Y.; "The Chemistry of Synthetic Dyes" vol. IV; pp. 218–223, 1971.

*Primary Examiner*—H. M. S. Sneed
*Attorney, Agent, or Firm*—Robert M. Hallenbeck

[57] ABSTRACT

Reticulocytes, RNA or DNA are stained with a dye for detection in a flow cytometer. The dye has the formula:

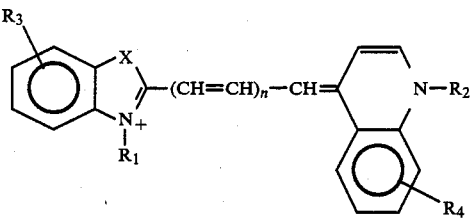

Wherein: X=O, S, Se, N -alkyl (having 1–6 carbons) or C $(CH_3)_n$;
  $R_1$=alkyl having from 1–6 carbons;
  $R_2$=alkyl having from 1–6 carbons;
  $R_3$=fused benzene, alkyl (having 1–6 carbons), methoxy or is absent;
  $R_4$=alkyl having 1–6 carbons, methoxy or is absent; and
  n=zero or an integer from 1–6.

15 Claims, 8 Drawing Sheets

FIG.1A
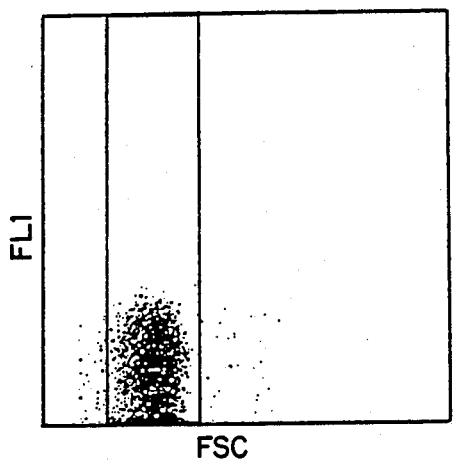
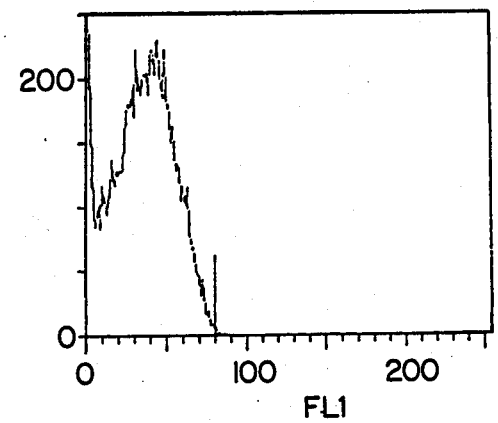
FIG.1B

FIG.2A
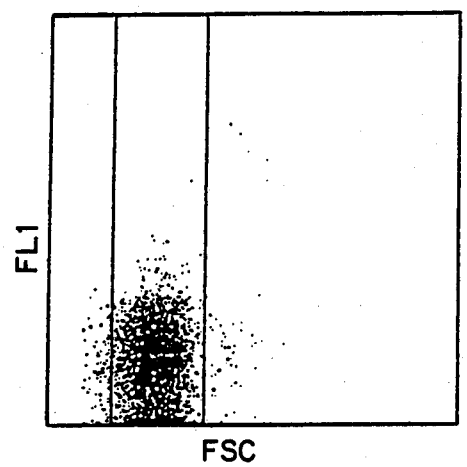
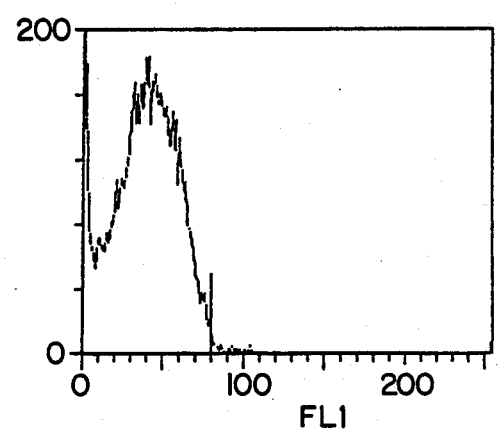
FIG.2B

DETECTION OF RETICULOCYTES, RNA OR DNA

The present application is a continuation-in-part of U.S. patent application Ser. No. 793,813, filed on Nov. 1, 1985 now abandoned.

BACKGROUND OF THE INVENTION

1. Field of the Invention

The present invention generally relates to the detection and enumeration of reticulocytes in a blood sample. More particularly, the present invention relates to a dye which is suitable for staining ribonucleic acid polymers (RNA) and deoxyribonucleic acid (DNA) and is particularly suitable for staining reticulocytes. The invention further relates to a fluorescent composition.

2. Description of the Prior Art.

In many cases, there is a need to detect RNA or RNA containing substances. Thus, for example, reticulocytes are a substance known to contain RNA, and detection and enumeration of reticulocytes in a blood sample are of value to clinicians. The reticulocyte count of a blood sample is used as an indicator of erythropoietic activity, has diagnostic and prognostic value in acute hemorrhage and hemolytic anemia, and is a measure response to iron, vitamin $B_{12}$ and folic acid therapy. As known in the art, reticulocytes are precursors to mature red blood cells, and hence the term reticulocyte embraces the evolution and development of the cell whereby a mature red blood cell is generated.

In the past, reticulocytes in a blood sample have been determined by both manual and automated methods by using appropriate stains such as new methylene blue (NMB), brilliant cresyl blue (BCB), acridine orange and pyronin Y.

Vital staining with the dye new methylene blue is considered to be the reference method for reticulocyte determinations, and in use this dye precipitates RNA. The method is manual, requires counting large numbers (for example, 500 to 1,000) of cells with a microscope, is slow, tedious, and subject to errors. New methylene blue is nonfluorescent and true precipitated RNA is often difficult to differentiate from precipitated stain.

Acridine orange has had some use in staining reticulocytes by both manual and automated procedures. Acridine orange also precipitates RNA, and this prevents quantitative estimates of RNA content because of potential quenching. Moreover, acridine orange does not lead to a diffuse fluorescent distribution of stained cells. Age profiles of the cells (based on RNA content being proportional to fluorescence) are not reliable. Acridine orange has a great affinity for the plastic tubing in flow cytometers which leads to increased background and lengthy procedures for removing the dye from the flow cytometer tubing. In addition, acridine orange stained cells are difficult to separate from the autofluorescent red cell peak, and the reticulocyte count is usually lower than that obtained with new methylene blue.

The use of pyronin Y requires prior fixation of the erythrocytes with formalin, is cumbersome, time consuming, and generally yields poor results. Moreover, pyronin Y has a very low quantum efficiency, leading to very low fluorescent signals.

U.S. patent application Ser. No. 460,144 filed Jan. 24, 1983, now U.S. Pat. No. 4,571,388 relates to a method for detecting reticulocytes utilizing thioflavin T as a dye for staining reticulocytes.

A dye for staining reticulocytes preferably has the following properties:

1. The dye should not fluoresce in the absence of RNA.
2. The dye should have a good fluorescent quantum yield.
3. The dye must be able to penetrate the membrane of cells containing RNA.
4. The dye should preferably have an excitation peak at about 488 nm.

None of the aforementioned known dyes for RNA and reticulocytes have all of the desirable features described hereinabove.

Accordingly, there is a need for providing a dye better suited for staining reticulocytes so as to provide a procedure for accurately determining reticulocytes in a blood sample.

In accordance with one aspect of the present invention, there is provided an improvement in a process for detecting reticulocytes wherein the reticulocytes are stained with a dye having the following formula:

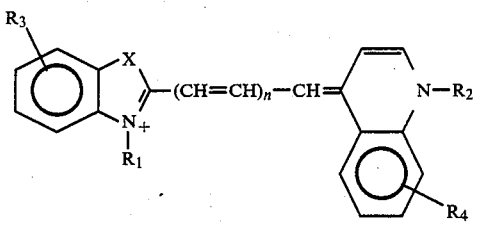

Wherein: X=O, S, Se, or C$(CH_3)_n$;
R$_1$=alkyl having from 1-6 carbons;
R$_2$=alkyl having from 1-6 carbons;
R$_3$=fused benzene, alkyl (having 1-6 carbons, methoxy or is hydrogen;
R$_4$=alkyl having 1-6 carbons, methoxy or is hydrogen; and
n=zero or an integer from 1-6

In accordance with another aspect of the present invention, reticulocytes are detected in a flow cytometer after the reticulocytes have been stained with the dye of the invention.

In accordance with a further aspect of the present invention, there is provided a composition comprised of reticulocytes stained with the dye of the invention.

The dye of the invention differs structually from thioflavin T. Thioflavin T has the following structure:

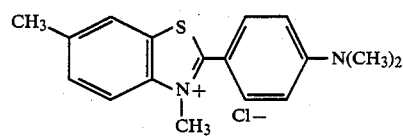

For convenience in the description hereinbelow and to describe a preferred embodiment of the invention, the dye of the invention for staining reticulocytes where R$_1$=R$_2$=CH$_3$; R$_3$=R$_4$=H, X=S and n=0 is referred to as "thiazole orange".

Applicant has found that thiazole orange is an effective dye for staining reticulocytes. The use of thiazole orange offers the further advantage that thiazole orange when unbound to ribonucleic acid provides little or no fluorescence, whereas thiazole orange when bound to ribonucleic acid in the reticulocytes is fluorescent. Thiazole orange can be excited at 488 nm whereas thioflavin T is excited at a maximum of about 455 nm.

In accordance with the present invention, when staining reticulocytes in a blood sample, the dyes of the invention may be employed as an aqueous solution, and in particular as an isotonic saline solution, which may contain a minor amount of methanol. The blood sample, which may be whole blood or a blood fraction, is stained with the dye by mixing the blood sample with the solution of thiazole orange. It has been found that by using thiazole orange as the stain, it is possible to detect and enumerate reticulocytes in a whole blood sample.

The dyes of the invention exhibit a strong absorption peak (unbound) in the range of from about 470 nm to about 600 nm; however, in the unbound state, the dye does not provide either a detectable excitation or emission peak. When thiazole orange stains the RNA in the reticulocytes, the optical properties thereof change dramatically. In particular, the absorption curve shifts to a longer wavelength, and the dye now exhibits strong fluorescence. For thiazole orange, the excitation maximum is at about 510 nm, and the emission maximum is at about 530 nm, giving a Stokes shift of about 20 nm. As a result of the excitation peak of the bound dye being in the order of about 510 nm, in using the automatic flow cytometer, the light source may be a mercury lamp which has an energy line at about 485 nm or an argon ion laser which has strong emission at 488 nm. The lack of fluorescence of the dye when not bound to nucleic acid provides low backgrounds and allows an operator to select a fluorescent threshold (or "gates") for an automatic flow cytometer by simply running an unstained control. Although excitation may be effected at other wavelengths, the thiazole orange stained reticulocytes are preferably excited at a wavelength of from about 460 nm to about 520 nm.

The dyes of the invention do not precipitate RNA, and as a result, the stained reticulocyte cells maintain a relatively homogeneous distribution of intracellular RNA, whereby there is a nearly linear relationship between the fluorescent signal measured for an individual reticulocyte and its RNA content. Clinically, this provides the physician with additional information beyond the reticulocyte count in that RNA content is a function of reticulocyte age. Accordingly, by using a dye of the invention, a clinician has the ability to do reticulocyte age profiles as well as simple reticulocyte counts.

The use of dyes of the invention for staining reticulocytes in a blood sample offers the further advantage that the fluorescent signals from the stained reticulocytes are well separated from those of the mature erythrocytes, whereby results can be directly read in an automatic low cytometer without extensive data manipulation.

Reticulocytes, RNA or DNA stained with a dye of the invention, although preferably enumerated in an automatic flow cytometer, can also be counted by a manual procedure or automated microscopy.

Automatic flow cytometers are well known in the art, and the present invention is not limited to the use of any particular flow cytometer. Thus, for example, thiazole orange stained reticulocytes may be detected and enumerated in the FACS 440 TM flow cytometer or the FACS Analyzer TM flow cytometer, both sold by Becton Dickinson and Company. In using such automatic flow cytometers, fluorescent gates are set by use of an unstained control sample, and the fluorescent gates are then used on the stained sample.

The use of an automatic flow cytometer for detection and enumeration of reticulocytes stained with thiazole orange provides results which closely correlate with results obtained by a known standard method for enumerating reticulocytes which uses methylene blue or acridine orange.

The use of reticulocytes stained with thiazole orange in an automatic flow cytometer is particularly advantageous in that there are low fluorescent backgrounds and fluorescent gates may be easily selected by use of an unstained control. Moreover, there is no precipitation of intracellular reticulocyte RNA, whereby the cells need not be fixed. In addition, there is a linear relationship between the fluorescent signal for an individual reticulocyte, which provides information as to reticulocyte age.

Still another advantage of the present invention is that thiazole orange stained reticulocytes can be used in an automatic flow cytometer having lower sensitivities, e.g., one may use a mercury arc lamp as opposed to an argon laser.

Although *Flow Cytometry and Sorting*, pages 457–58 Edited by Melamed et al., John Wiley & Sons, describes the use of both acridine orange and thioflavin T for staining RNA of living cells, this publication does not disclose the use of the dyes of the invention as a stain for reticulocyte detection and enumeration in an automatic flow cytometer.

The following example illustrates various features of the present invention but is not intended to in any way limit the scope of the invention as set forth in the claims.

EXAMPLE 1

A dye of the invention wherein $R_1$ and $R_2=CH_3$, $X=S$ $n=0$ and $R_3$ and $R_4$ are hydrogen (thiazole orange) was used in a procedure for reticulocyte staining.

A 1 mg/ml stock solution of the dye in methanol was prepared. A 1:8,000 dilution of the stock solution in pH 7.2 phosphate buffered saline was made, 5 uL of whole blood was mixed into 1 mL of the diluted dye solution. The sample was analyzed on a FACS 440 TM flow cytometer with an excitation wavelength of 488 nm and a 530/30 nm bandpass filter.

Figure 3B:
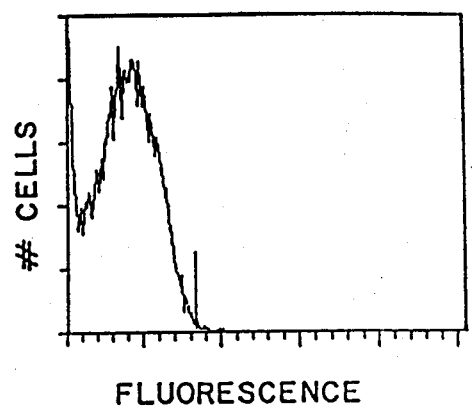
Figure 4A:
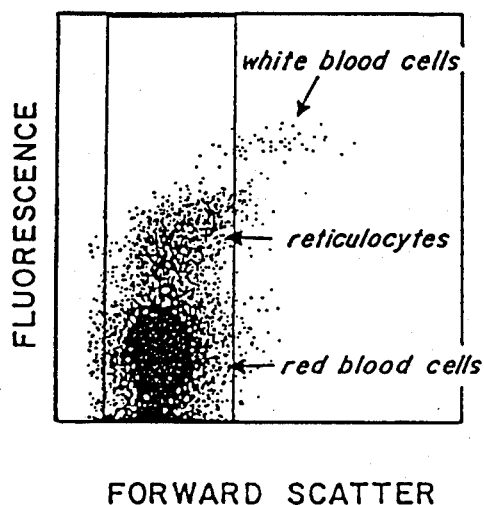
Figure 4B:
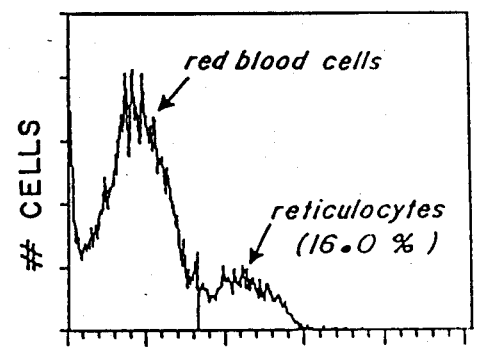
Figure 5A:
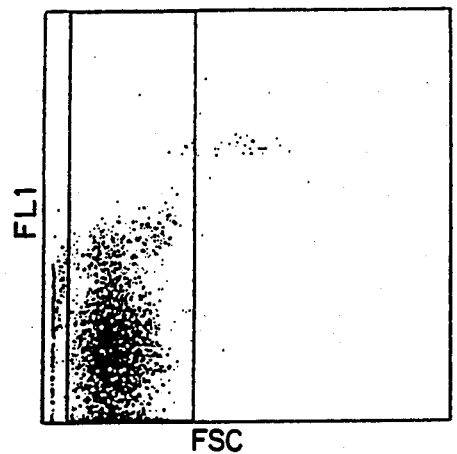
Figure 5B:
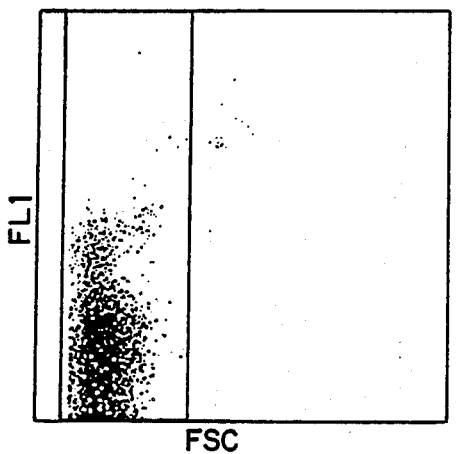
Figure 5C:
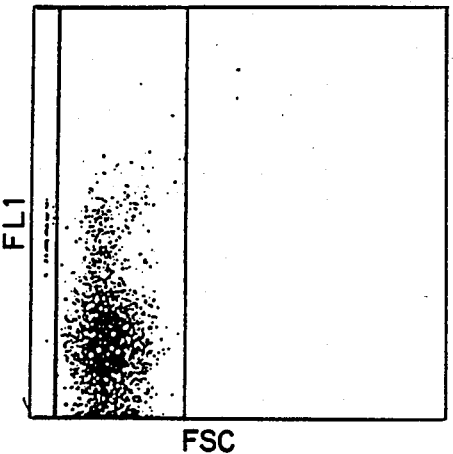
Figure 6:
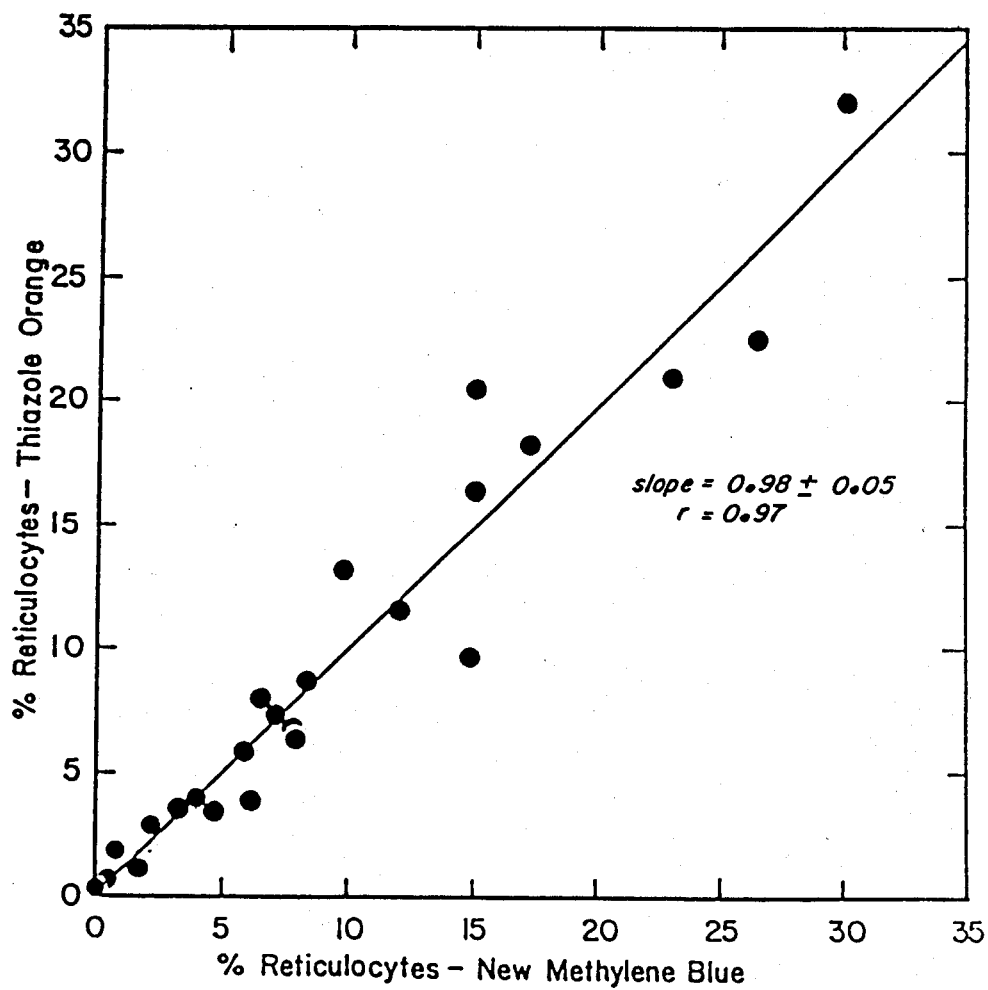

FIGS. 1-6 show FACS data for reticulocyte analysis of normal and anemic blood using thiazole orange of this example. FIG. 1 shows a fluorescence histogram (FIG. 1B) and fluorescence vs. forward scatter (FIG. 1A) for normal, unstained blood. FIG. 2 shows a fluorescence histogram (FIG. 2B) and fluorescence vs. forward scatter (FIG. 2A) for normal blood stained with thiazole orange. FIG. 3 shows a fluorescence histogram (FIG. 3B) and fluorescence vs. forward scatter (FIG. 3A) for unstained anemic blood (17.3% reticulocytes by new methylene blue assay). FIG. 4 shows a fluorescence histogram (FIG. 4B) and fluorescence vs. forward scatter (FIG. 4A) for the anemic blood after staining. FIG. 5 shows samples of anemic blood (8.4% reticulocytes by new methlyene blue assay) stained with thiazole orange of this example for varying lengths of time: 30 minutes (FIG. 5A), 70 minutes (FIG. 5B) and 7 hours (FIG. 5C). analysis with new methylene blue and flow cytometry analysis using thiazole orange.

Figure 7:
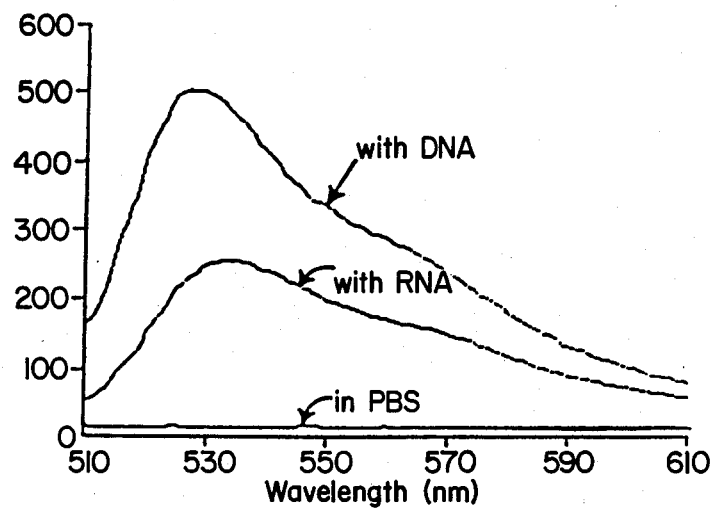

Thiazole orange is shown to be fluorescent only when bound to nucleic acid polymers. FIG. 7 shows fluorescence emission spectra of thiazole orange with DNA, RNA and in phosphate buffered saline (PBS) which was free of nucleic acids.

A solution of thiazole orange in DMSO was prepared ($5 \times 10^{-3}$M). The solution was diluted into PBS ($5 \times 10^{-5}$M). A cuvette containing 30 uL of the thiazole orange solution, 90 uL of DNA solution (1 mg/mL) and 2.88 mL of PBS was mixed and the fluorescence emission spectrum measured on a Perkin-Elmer MPF-2A fluorescence spectrophotometer. The excitation wavelength was 500 nm and the emission was measured from 510 to 610 nm. A cuvette containing 30 uL of the thiazole orange solution, 50 uL of RNA (1 mg/mL) and 2.92 mL PBS was mixed and the fluorescence emission spectrum measured in the same way as described above. A cuvette containing 30 uL of the thiazole orange solution and 2.97 mL PBS was mixed and the fluorescence emission spectrum measured.

EXAMPLE 2

Figure 8:
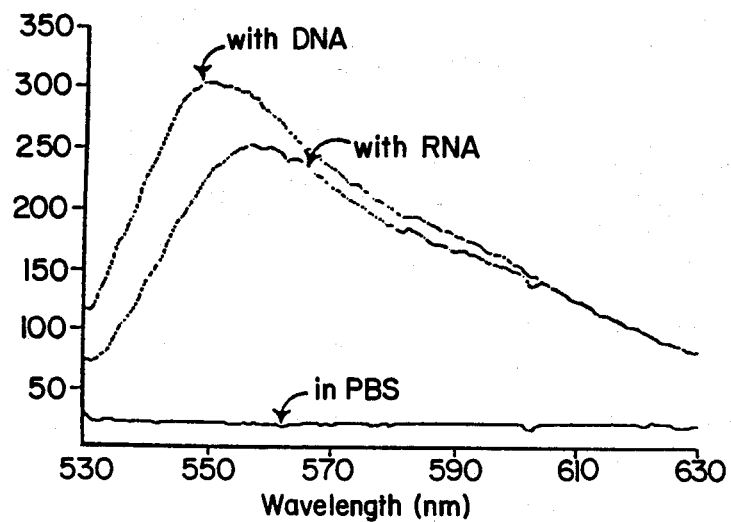

A dye wherein $R_1=R_2=CH_3$, $R_3=$fused benzene, $R_4=H$, $X=S$ and $n=0$ (thiazole red), was shown to be fluorescent only in the presence of nucleic acid polymers. FIG. 8 shows fluorescence emission spectra of thiazole red with DNA, RNA and in PBS. The spectra were obtained in the same way as described in Example 1 except the excitation wavelength was 520 nm and the emission spectra were measured from 530 to 630 nm. The structure of thiazole red is:

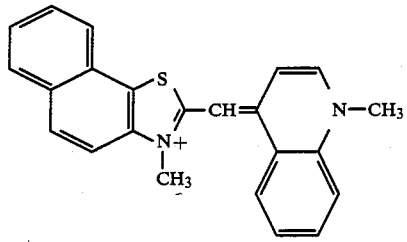

EXAMPLE 3

Figure 9:
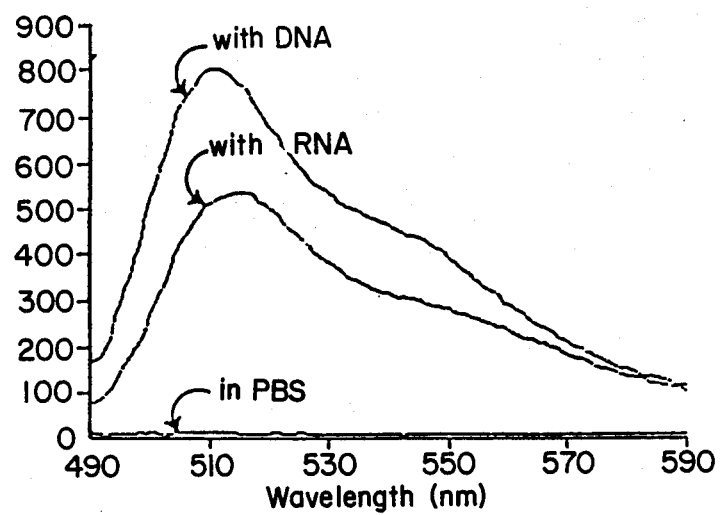

A dye wherein $R_1=R_2=CH_3$, $R_3=R_4=H$, $X=O$ and $n=0$ (methyl oxazole yellow), was shown to be fluorescent only when bound to nucleic acid polymers. FIG. 9 shows fluorescence emission spectra of methyl oxazole yellow with DNA, RNA and in PBS. The spectra were obtained in the same way as described in Example 1 except the excitation wavelength was 480 nm and the emission spectra were measured from 490 to 590 nm. The structure of methyl oxazole yellow is:

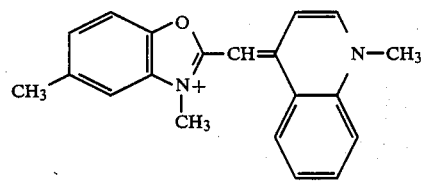

EXAMPLE 4

Figure 10:
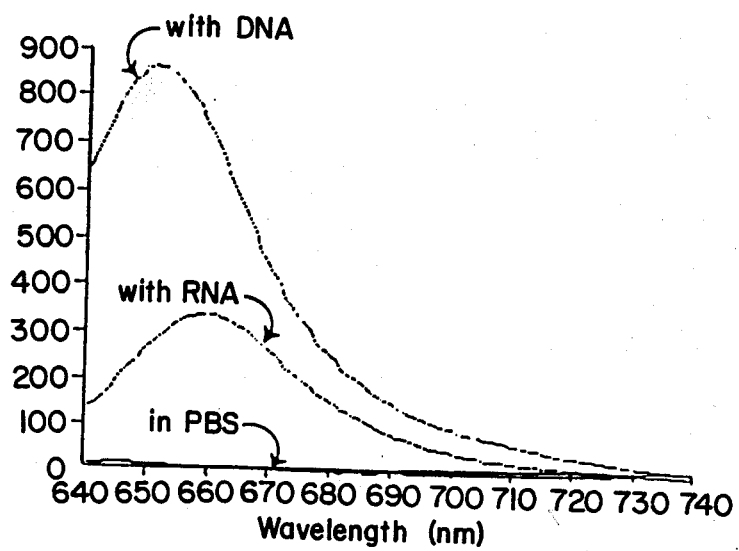

A dye wherein $R_1=R_2=CH_3$, $R_3=R_4=H$, $X=S$ and $n=1$ (thiazole blue), was shown to be fluorescent only in the presence of nucleic acid polymers. FIG. 10 shows fluorescence emission spectra of thiazole blue with DNA, RNA and in PBS. The spectra were obtained in the same way as described in Example 1 except the excitation wavelength was 630 and the emission spectra were measured from 640 to 740 nm.

EXAMPLE 5

Figure 11:
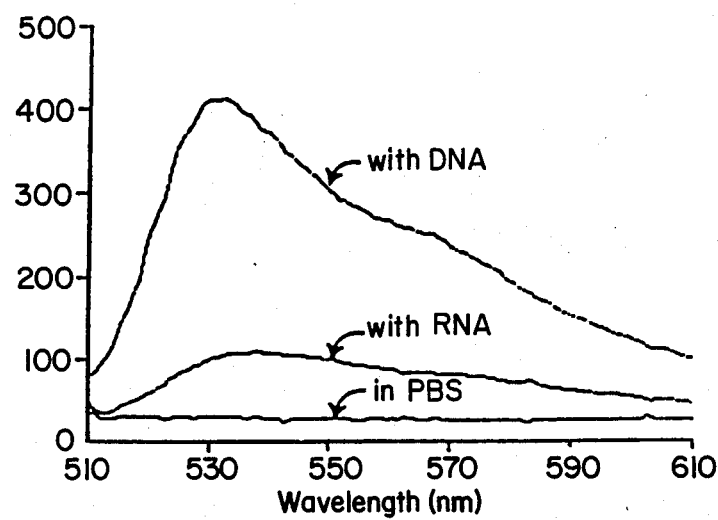

A dye wherein $R_1=R_2=CH_2CO_2H$, $R_3=R_4=H$, $X=S$ and $n=0$ (thiazole orange dicarboxylate), was shown to be fluorescent only when bound to nucleic acid polymers. FIG. 11 shows fluorescence emission spectra of thiazole orange dicarboxylate with DNA, RNA and in PBS. The spectra were obtained in the same way as described in Example 1.

EXAMPLE 6

Figure 12:
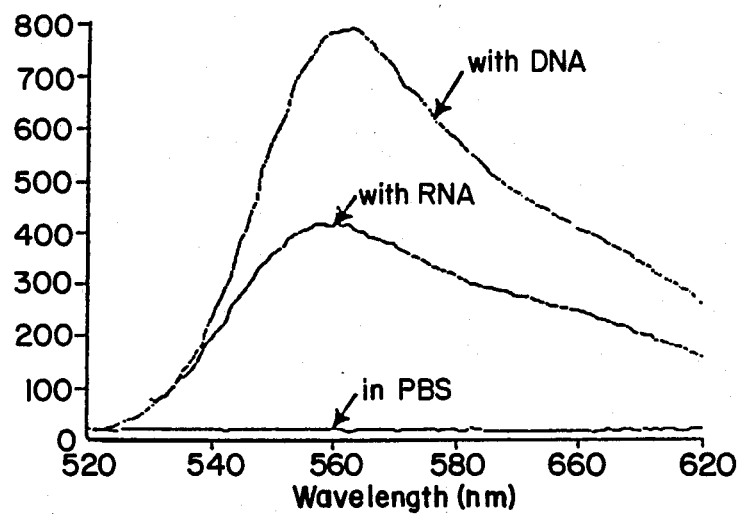

A dye wherein $R_1=R_2=CH_3$, $R_3=R_4=OCH_3$, $X=S$ and $n=0$ (dimethoxy thiazole orange), was shown to be fluorescent only when bound to nucleic acid polymers. FIG. 12 shows fluorescence emission spectra of dimethoxy thiazole orange with DNA, RNA and in PBS The spectra were obtained in the same way as described in Example 1 except the excitation wavelength was 510 nm and the emission spectra were measured from 520 to 620 nm. The structure of dimethoxy thiazole orange is:

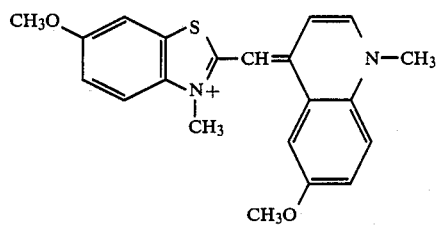

Numerous modifications and variations of the present invention are possible in light of the above teachings, and, therefore, are within the scope of the appended claims. The invention may be practiced otherwise than as particularly described.

What is claimed is:

1. A compound composed of reticulocytes bound to a dye having the formula:

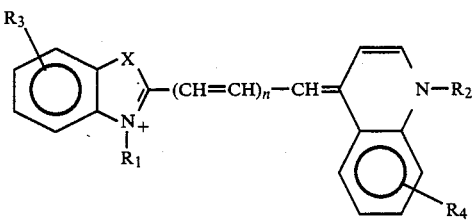

Wherein: $X=O, S, Se$ or $C(CH_3)_2$:
  $R_1=$alkyl having from 1-6 carbons;
  $R_2=$alkyl having from 1-6 carbons;
  $R_3=$fused benzene, alkyl (having 1-6 carbons), methoxy or hydrogen;
  $R_4=$alkyl having 1-6 carbons, methoxy or hydrogen; and
  $n=$zero or an integer from 1-6.

2. A compound of claim 1 wherein $R_1=CH_3$, $R_2=CH_3$, $R_3=$hydrogen, $R_4=$hydrogen, $X=S$ and $n=1$.

3. A compound in accordance with claim 1 wherein $R_1=CH_3$, $R_2=CH_3$, $R_3=$fused benzene, $R_4=$hydrogen, $X=S$ and $n=0$.

4. A compound in accordance with claim 1 wherein $R_1=CH_3$, $R_2=CH_3$, $R_3=$hydrogen, $R_4=$hydrogen, $X=O$ and $n=$zero.

5. A compound composed of RNA bound to a dye having the formula:

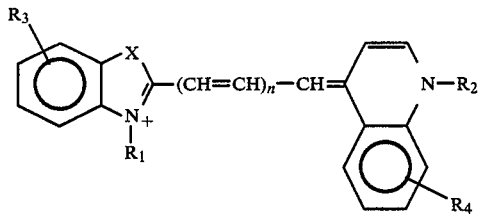

Wherein: $X=O, S$, Se or $C(CH_3)_2$:
- $R_1=$alkyl having from 1-6 carbons;
- $R_2=$alkyl having from 1-6 carbons;
- $R_3=$fused benzene, alkyl (having 1-6 carbons), methoxy or is hydrogen;
- $R_4=$alkyl having 1-6 carbons, methoxy or hydrogen; and
- $n=$zero or an integer from 1-6.

6. A compound in accordance with claim 5 wherein $R_1=CH_3$, $R_2=CH_3$, $R_3=$hydrogen, $R_4=$hydrogen, $X=S$, and $n=1$.

7. A compound in accordance with claim 5 wherein $R_1=CH_3$, $R_2=CH_3$, $R_3=$fused benzene, $R_4=$hydrogen, $X=S$ and $n=0$.

8. A compound in accordance with claim 5 wherein $R_1=CH_3$, $R_2=CH_3$, $R_3=$hydrogen, $R_4=$hydrogen, $X=O$ and $n=$zero.

9. A compound composed of DNA bound to a dye having the formula:

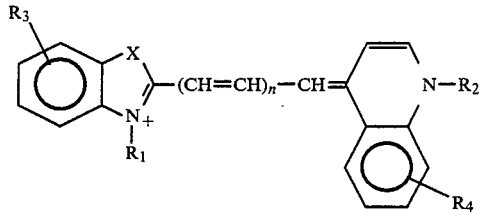

wherein: $X=O, S$, Se or $C(CH_3)_2$;
- $R_1=$alkyl having from 1-6 carbons;
- $R_2=$alkyl having from 1-6 carbons;
- $R_3=$fused benzene, alkyl (having 1-6 carbons), methoxy or is hydrogen;
- $R_4=$alkyl having 1-6 carbons, methoxy or hydrogen; and
- $n=$zero or an integer from 1-6.

10. A compound in accordance with claim 9 wherein $R_1=CH_3$, $R_2=CH_3$, $R_3=$hydrogen, $R_4=$hydrogen, $X=S$ and $n=1$.

11. A compound in accordance with claim 9 wherein $R_1=CH_3$, $R_2=CH_3$, $R_3=$fused benzene, $R_4=$hydrogen, $X=S$ and $n=0$.

12. A compound in accordance with claim 9 wherein $R_1=CH_3$, $R_2=CH_3$, $R_3=$hydrogen, $R_4=$hydrogen, $X=O$ and $n=$zero.

13. A compound in accordance with claim 9 wherein $R_1=CH_3$, $R_2=CH_3$, $R_3=$hydrogen, $R_4=$hydrogen, $X=S$ and $n=1$.

14. A compound in accordance with claim 9 wherein $R_1=CH_2C_2H_5$, $R_2=CH_2CH_3$, $R_3=$hydrogen, $R_4=$hydrogen, $X=S$ and $n=0$.

15. A compound in accordance with claim 9 wherein $R_1=CH_3$, $R_2=CH_3$, $R_3=OCH_3$, $R_4=OCH_3$, $X=S$ and $n=0$.

* * * * *